United States Patent [19]

Batchelder et al.

[11] Patent Number: 4,844,613
[45] Date of Patent: Jul. 4, 1989

[54] OPTICAL SURFACE PLASMON SENSOR DEVICE

[75] Inventors: David N. Batchelder, London; Jolyon P. Willson, Duxford, both of Great Britain

[73] Assignee: STC PLC, London, England

[21] Appl. No.: 115,766

[22] Filed: Nov. 2, 1987

[30] Foreign Application Priority Data

Nov. 3, 1986 [GB] United Kingdom ............... 8626221

[51] Int. Cl.⁴ ...................... G01N 21/55; G01N 21/63
[52] U.S. Cl. ..................................... 356/318; 356/445
[58] Field of Search ............... 356/311, 317, 318, 445

[56] References Cited

U.S. PATENT DOCUMENTS 3,984,189 10/1976 Seki et al. ............................ 356/446
4,681,451 7/1987 Guerra et al. ....................... 356/373

FOREIGN PATENT DOCUMENTS 2173895 10/1986 United Kingdom ............... 356/318

Primary Examiner—Vincent P. McGraw
Attorney, Agent, or Firm—Lee & Smith

[57] ABSTRACT

An optical sensor device uses surface plasmon resonance to detect the presence of a specific material. A transparent body (12) is coated with a thin gold film (14) which film may be coated e.g. with an antibody material. The arrangement is illuminated with a divergent light beam and light internally reflected from the gold film is detected by a photodiode array (16). The dielectric conditions adjacent the gold film determine the position of the surface resonance angle, this being indicated by a dark area on the detector array.

7 Claims, 2 Drawing Sheets

4,844,613

OPTICAL SURFACE PLASMON SENSOR DEVICE

This invention relates to optical sensors, e.g. for chemical, biochemical or biological analysis.

BACKGROUND OF THE INVENTION

Surface plasmon resonance is an optical surface phenomenon that has recently been employed in the construction of sensors. A surface plasmon is a surface charge density wave at a metal surface. A physical description of the phenomenon is given by H. Raether in Phys. Thin Films, 1977, 74 pp 237-244. The resonance can be observed when the evanescent field of a p-polarised light beam, totally internally reflected from a dielectric interface, interacts with a thin metal film applied to the interface. Typically the interface comprises a smooth surface of a transparent, e.g. glass, body. Light reflected internally from the surface exhibits a minimum intensity for a particular (resonant) angle of incidence, this angle being determined by the dielectric conditions adjacent the metal film and the properties of the metal film itself.

Plasmon resonance is observed when the component of the evanescent field wave vector parallel to the metal/dielectric interface ($K_x$) is equal to the surface plasmon wave vector ($K_{sp}$) as given by the following equation:

$$K_x = \frac{W}{C} \sqrt{\epsilon_1} \sin\theta = K_{sp} = \frac{W}{C}\left(\frac{1}{\epsilon_2} + \frac{1}{\epsilon_m}\right)^{-\frac{1}{2}}$$

where W is the optical frequency, C the free space velocity of light and $\epsilon_m$ is the real part of the dielectric constant of the metal. $\epsilon_1$ is the dielectric constant of the prism and $\epsilon_2$ is the dielectric constant of a dielectric applied to the metal. $\theta$ is the angle of incidence of the optical beam at the metal/dielectric interface. Thus the value of the wave vector at resonance is a function of both dielectric constants, the optical wavelength and of the metal.

In a prior art sensor using this phenomenon, a metal film is applied to one surface of a glass prism. Such a device is described in Electronics Letters, 8th Nov. 1984, 20, No. 23, pp 968 to 970. In this device the resonant angle is determined by varying the angle of incidence of light directed through the prism to the surface and measuring the intensity of the reflected light. Such an arrangement requires a high degree of precision in the manufacture of its optical moving parts to provide accurate measurement.

The object of the present invention is to minimise or to overcome this disadvantage.

SUMMARY OF THE INVENTION

According to the invention there is provided an optical sensor device, the device including a transparent body having a major surface, a thin conductive film supported on said surface, means for directing a divergent light beam through the body towards said surface so as to excite surface plasmons in the conductive film, and means for detecting the pattern of light reflected internally from the major surface so as, in use, to determine the angle or angles of incidence at which plasmon resonance occurs.

As there are no moving parts the problem of high precision manufacture is alleviated. Typically the reflected light pattern is detected via a photodetector array e.g. of the type employed in a television camera tube. Typically the transparent body is formed of glass on a plastics material.

An embodiment of the invention will now be described with reference to the accompanying drawings in which:

DESCRIPTION OF PREFERRED EMBODIMENT

Figure 1:
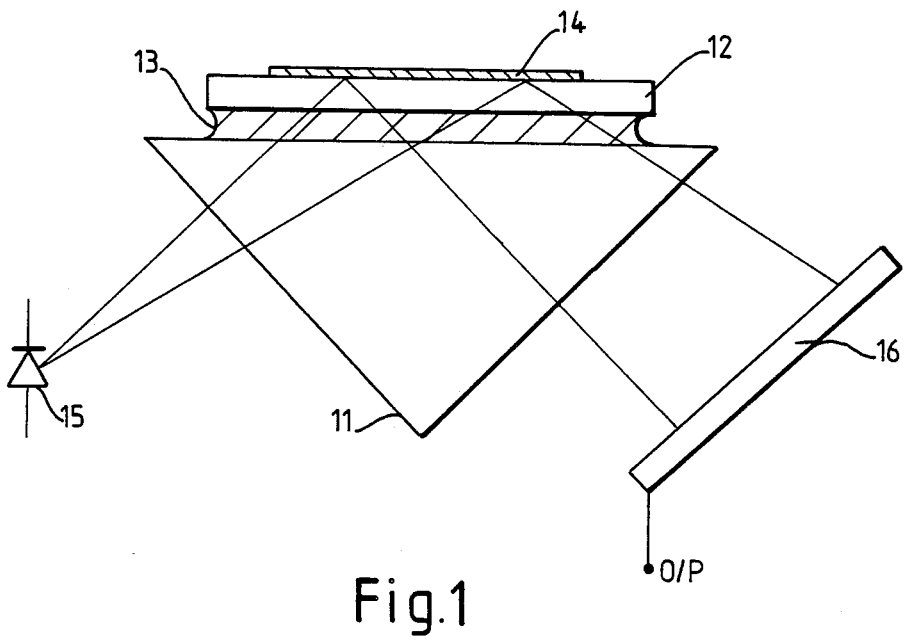
FIG. 1 is a sectional schematic view of the surface wave plasmon sensor device.

Referring to FIG. 1, the sensor device includes a transparent prism 11, e.g. of equilateral triangular cross-section, on the surface of which is mounted a glass microscope slide or cover slip 12. The airgap between the slide 12 and the prism 11 is filled with a quantity of index matching fluid 13. Where the prism 11 is of glass we prefer to employ glycerol ($n=1.47$) as the index matching fluid. The upper surface of the slide 12 is coated with a thin conductive layer 14 e.g. gold, typically 400 to 700 A (40 to 70 nm) in thickness. This layer 14 provides the conductive surface layer in which, in use, surface plasmons are excited.

Light is directed to the prism assembly from a light source 15 comprising e.g. a light emitting diode. Advantageously the light source 15 has an output wavelength in the range 500 nm to 900 nm. The light from the source 15 is incident on the prism in the form of a divergent beam. This beam, after refraction at the glass/metal interface passes back through the prism 11 to a detector array 16. The image 'seen' by the array comprises a substantially uniformly illuminated area with a dark band corresponding to the angle or angles at which plasmon resonance reduces the intensity of reflected light. The position of the absorption band may be determined by a microprocessor (not shown) coupled to the detection array 16.

The angular position of the plasmon resonance is a function of the dielectric constant of a medium in contact with the gold film 14. As the electric field associated with the plasmon decays exponentially into the medium, the device is sensitive only to changes close to the gold surface, typically within 1000 Augstroms. In general the device is used in chemical or biological applications to detect species present in aqueous solutions, e.g. blood serum, whose refractive index is 1.33 to 1.35. For biosensing applications the gold film 14 may be coated with a layer, typically 50 to 100 A thick, of an antibody whose refractive index is 1.5 to 1.6. As the refractive index of the antibody layer differs from that of the adjacent solution, a change in the antibody layer thickness emitting from bonding sheets of a corresponding antigen causes a corresponding change in the plasmon resonance angle. Typically the sensitivity of the device is such that a change of 1A in the antibody layer thickness causes a change of 0.01° in the resonance angle for a source wavelength of 820 nm.

The sensitivity of the device may be improved by the use of a light source of short wavelength so that the plasmon penetration depth is then smaller. For example, a source wavelength of 560 nm gives a sensitivity of about 0.1°/A. However, it should be noted that, if lower sensitivity can be tolerated, working at longer wavelengths is to be preferred as, at such wavelength, the spectral line width (10-50 nm) of LED sources does not unduly broaden the angular width of the resonance. At short wavelengths this effect can be mitigated by the use of a narrow band filter or by the use of a gas laser as the light source. For example, a helium/neon gas laser has suitable output wavelength at 543 nm and 594 nm.

In an alternative arrangement a pair of similar light sources may be employed. One light source is used to provide sensing whilst the other provides a reference channel to compensate e.g. for non-specific binding effects. The light sources and sample sites are arranged so that the reflected divergent beams are both received by the photodiode array. By selectively enabling the light sources the plasmon resonance angle can be accurately measured for two sample sites only one of which is coated with the antibody. The difference in plasmon resonance angle is then due solely to specific binding effects. For a more accurate cancellation of non-specific binding, the second site can be coated with a different antibody with similar dielectric characteristics, or a deposited dielectric film.

Figure 2:
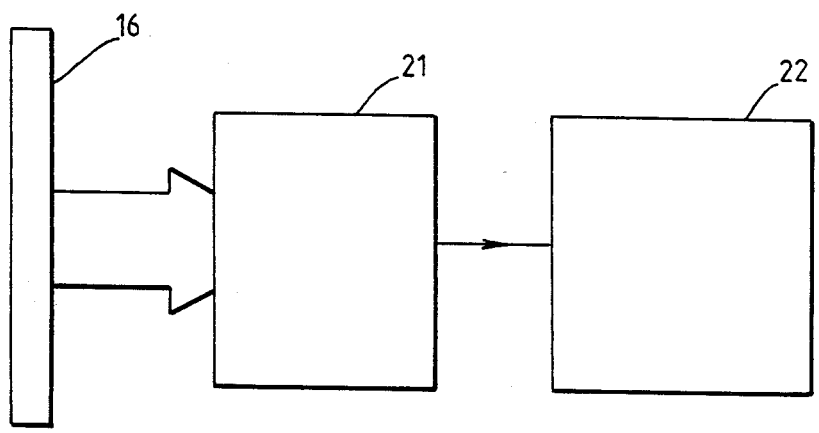
FIG. 2 shows a data processing system for use with the sensor of FIG. 1.

The accuracy of measurement of the sensor system of FIG. 1 may be enhanced by the use of a data aquisition arrangement. Such an arrangement is shown in FIG. 2 of the accompanying drawings. The operation of this data aquisition arrangement is described below with reference to a photodiode arrangement having 128 elements, but it will be clear that this description is given by way of example only, and that alternative arrangements may be employed.

The outputs of the photodiodes of the array are fed via a data aquisition module 21 to a computer 22. The computer determines the position of minimum light intensity, i.e. the plasma resonance angle, by a curve fitting process which identifies this minimum to a high degree of accuracy.

Figure 3:
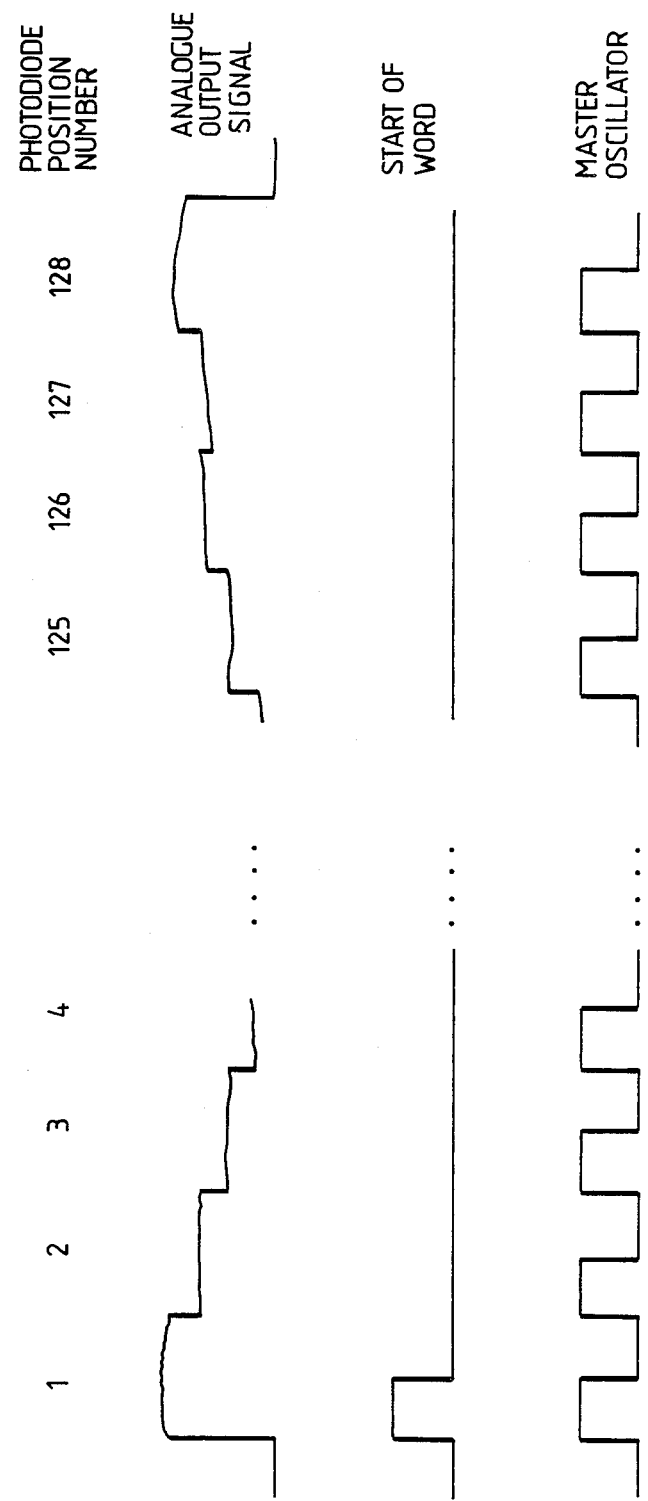
FIG. 3 illustrates data format waveforms used in the system.

The data aquisition module 21 provides the computer 22 with the following signals which are illustrated in FIG. 3 of the accompanying drawing:

(i) An analogue signal, which consists of a series of words where each word comprises 128 pulses and the height of each pulse corresponds to the intensity of the light falling on the corresponding photodiode.

(ii) A master oscillator signal which goes high at the beginning of each pulse in the analogue output signal.

(iii) A start of word signal which goes high at the beginning of each word of the analogue output signal. The master oscillator and therefore also the analogue output signal may have a frequency of about 10 kHz.

Processing of the input data is effected by the computer in a two stage process. Firstly, each input word is evaluated to determine the position at which the minimum light intensity occurs. Data corresponding to the outputs of the 40 photo detections measurement to this minimum position is then stored for analysis in the second stage of the process.

The second stage involves fitting of a polynomial, e.g. a fourth order polynomial, to the 40 readings obtained from the previous stage. The method used is to minimise the squares of the differences between the stored values and the values calculated for a general fourth order polynomial. Having obtained expressions for the spaces of the differences, these are used to form a system of linear homogeneous equations. This system of equations is solved by matrix inversion to give the desired polynomial. The characteristics of this polynomial are then evaluated to determine its turning points and thus to determine the precise position of the minimum value.

It is preferred that correction factors be applied to each element of the 128 element word to compensate for differences in the photo detector elements of the array.

It is known that each element of the array has a different dark-current and that each element becomes saturated at a different level of light intensity, i.e., the relationship between voltage output and light intensity is different for each element of the array, and they differ by at least two parameters. It is assumed that the relationship is linear and thus has exactly two parameters which can be calculated for each photodiode by taking two calibration readings. It is also assumed that for the Ith photodiode there exist numbers offset (I) and linmult (I) such that:

$$V_I = (L \times \text{limult}\ [I] + \text{offset}\ (I))$$

where $L$ = Light intensity on Ith photodiode and $V_I$ = Voltage od Ith pulse in analogue output signal word.

First, there is no light falling on the array, ten "words" are read from the photodiode array, and for each I an average height of the Ith pulse is calculated. These are the values of offset (I). Then when each photodiode in the array has the same light intensity falling on it, ten more "words" again are read fron the photodiode array and an average output for each array element is again calculated. An average of all the heights of all the pulses is also calculated (i.e., the average of 10 × 128 numbers) and this is assumed to be the true light intensity (i.e., L is the equation above). Thus for each I linmult (I) can be calculated using the formula.

$$\text{linmult}\ (I) = \frac{v - \text{offset}\ (I)}{L}$$

To illustrate the technique, a clear microscope slide was coated with a 45nm thick layer of gold. The gold surface was coated with a monolayer of thyroid stimulating hormone antibody. Half the slide area was then coated with a monolayer of thyroid stimulating hormone. The slide was mounted on a glass prism and covered with a water film. The arrangement was illuminate using a Honeywell (registered Trade Mark) Sweetspot LED source. The difference in plasmon resonance angle determined by measurements of the two halves of the slide was found to be 0.07°. This illustrates the facility of detection of biochemical materials using the arrangement described herein.

Although the sensor has been described with particular reference to biological or biochemical applications it can of course also be employed as a sensor in purely chemical applications.

We claim:

1. An optical sensor device, including a transparent body having a major surface on which a thin electrically conductive film is disposed, a light source fixed in position relative to the body and arranged to direct a divergent monochromatic light beam through the body to the surface whereby to achieve total internal reflection of the light from that surface and to excite surface plasmons in the conductive film, and an array of photodetectors arranged so as to detect the pattern of light reflected internally from the major surface whereby to determine the angle of incidence at that surface at which plasmon resonance occurs.

2. A sensor device as claimed in claim 1, wherein the conductive film comprises gold.

3. A sensor device as claimed in claim 2, wherein the conductive film is coated with a layer of an antibody.

4. A sensor device as claimed in claim 3, wherein the transparent body is formed of glass or a plastics material.

5. A sensor device as claimed in claim 4, wherein said transparent body comprises a laminar body supported on and in optical contact with a further transparent body.

6. A sensor device as claimed in claim 1, and incorporating a further reference light source.

7. An optical sensor arrangement, including a transparent body having a major surface on which a thin conductive film is disposed, means for directing a divergent monochromatic light beam through the transparent body towards said surface so as to excite surface plasmons in the conductive film, an array of photodetectors arranged so as to receive light reflected internally at a range of angles from the major surface, means for evaluating the intensity of light received from each photodetector, and means for calculating a polynomial corresponding to said light intensities whereby to determine the angle of reflection for which a minimum light intensity indicative of plasmon resonance is obtained.

* * * * *